(12) United States Patent
Jaguan

(10) Patent No.: US 10,098,811 B2
(45) Date of Patent: Oct. 16, 2018

(54) PORTABLE RELAXATION THERAPY MASSAGE DEVICE FOR THE HEAD

(71) Applicant: Mauro Jaguan, Caracas (VE)

(72) Inventor: Mauro Jaguan, Caracas (VE)

( * ) Notice: Subject to any disclaimer, the term of this patent is extended or adjusted under 35 U.S.C. 154(b) by 399 days.

(21) Appl. No.: 14/428,941

(22) PCT Filed: Sep. 11, 2014

(86) PCT No.: PCT/US2014/055257
§ 371 (c)(1),
(2) Date: Mar. 17, 2015

(87) PCT Pub. No.: WO2015/038821
PCT Pub. Date: Mar. 19, 2015

(65) Prior Publication Data
US 2016/0271013 A1    Sep. 22, 2016

Related U.S. Application Data

(60) Provisional application No. 61/877,250, filed on Sep. 12, 2013.

(51) Int. Cl.
*A61H 35/00* (2006.01)
*A61N 5/06* (2006.01)
(Continued)

(52) U.S. Cl.
CPC .......... *A61H 35/008* (2013.01); *A61H 33/06* (2013.01); *A61M 21/02* (2013.01); *A61N 5/0618* (2013.01); *A61H 2009/0042* (2013.01); *A61H 2033/0037* (2013.01); *A61H 2033/0083* (2013.01); *A61H 2201/10* (2013.01); *A61H 2201/102* (2013.01);
(Continued)

(58) Field of Classification Search
CPC .. A61H 33/00; A61H 33/0087; A61H 33/066; A61H 33/6021; A61H 33/6057; A61H 33/6031; A61H 33/6036; A61H 35/00; A61H 35/008; A61H 2009/0035; A61H 2009/0042; A61H 9/00; A61H 9/0028; A61H 2205/021; A61H 7/006; A61H 2201/102; A61N 2005/0663; A61N 2005/0647; A61N 2005/0662; A61N 2005/0643; A61N 2005/0651; A61N 2005/0652; A61N 2005/0653; A61N 2005/0654; A61F 7/0053; A45D 19/14; A45D 19/08; A45D 2007/008;
(Continued)

(56) References Cited

U.S. PATENT DOCUMENTS 3,343,530 A * 9/1967 Solos ............... A45D 19/14
                                                    132/202
3,400,248 A * 9/1968 Isomaa ............ A61H 33/063
                                                    126/344
(Continued)

*Primary Examiner* — Michael Tsai
*Assistant Examiner* — Christopher Miller

(57) ABSTRACT

The present invention administers fluid therapy and chromotherapy to the head of a user for stimulatory purposes. Particularly, the invention comprises a portable device for administering fluid therapy using pressurized water and/or other therapeutic fluids and/or substances to massage and relax the head and scalp of the user while simultaneously allowing the use of craniofacial chromotherapy thus providing a generally relaxing and refreshing stimulative experience for the head.

9 Claims, 6 Drawing Sheets

(51) Int. Cl.
*A45D 19/00* (2006.01)
*A61H 33/06* (2006.01)
*A61M 21/02* (2006.01)
*A61H 9/00* (2006.01)
*A61H 33/00* (2006.01)
*A61M 21/00* (2006.01)

(52) U.S. Cl.
CPC ............... *A61H 2201/107* (2013.01); *A61H 2203/0456* (2013.01); *A61M 2021/0016* (2013.01); *A61M 2021/0027* (2013.01); *A61M 2021/0044* (2013.01); *A61M 2205/051* (2013.01); *A61N 2005/063* (2013.01); *A61N 2005/0626* (2013.01); *A61N 2005/0643* (2013.01); *A61N 2005/0652* (2013.01); *A61N 2005/0663* (2013.01)

(58) Field of Classification Search
CPC ............... A45D 44/02; A45D 44/10; A45D 2019/0033; A45D 2019/0041; A45D 2019/0058; A45D 19/04
See application file for complete search history.

(56) References Cited

U.S. PATENT DOCUMENTS

| | | | | |
|---|---|---|---|---|
| 3,521,647 A | * | 7/1970 | Mercer | A45D 19/14 132/272 |
| 4,340,981 A | * | 7/1982 | Vanags | A61H 33/06 4/524 |
| 4,384,190 A | * | 5/1983 | Janson | A61H 33/063 236/51 |
| 4,407,028 A | * | 10/1983 | Nolan | A45D 19/14 4/516 |
| 5,387,178 A | * | 2/1995 | Moses | A47C 21/003 600/27 |
| 5,848,444 A | * | 12/1998 | Christopherson | A61H 33/027 239/587.3 |
| 5,891,186 A | * | 4/1999 | Daffer | A61H 23/02 600/21 |
| 5,953,770 A | * | 9/1999 | Kitamura | A61H 9/00 4/596 |
| 5,978,983 A | * | 11/1999 | Queen | A47K 3/006 4/555 |
| 6,539,561 B2 | * | 4/2003 | Shimizu | A47K 3/001 362/101 |
| 6,623,511 B1 | * | 9/2003 | Daffer | A61F 7/0053 128/898 |
| 6,702,767 B1 | * | 3/2004 | Douglas | A61M 21/0094 600/21 |
| 7,191,474 B2 | * | 3/2007 | Matsunaga | A45D 19/14 4/515 |
| 7,384,165 B2 | * | 6/2008 | Doyle | B05B 15/00 362/101 |
| 7,427,840 B2 | * | 9/2008 | Morgan | F21V 33/004 315/295 |
| 7,537,576 B1 | * | 5/2009 | Worley, III | A61H 1/001 601/46 |
| 7,810,179 B2 | * | 10/2010 | Fujikawa | A45D 19/10 4/515 |
| 2002/0141889 A1 | * | 10/2002 | Toye | A61H 33/6063 417/366 |
| 2003/0000010 A1 | * | 1/2003 | Shimizu | A61H 33/026 4/541.5 |
| 2003/0070222 A1 | * | 4/2003 | Bastia | A61H 9/00 4/622 |
| 2003/0147241 A1 | * | 8/2003 | Hildebrand | A61H 33/6063 362/231 |
| 2003/0172721 A1 | * | 9/2003 | Brunelle | A61N 5/0618 73/52 |
| 2004/0034918 A1 | * | 2/2004 | Loyd | A61H 33/0087 4/541.1 |
| 2004/0059184 A1 | * | 3/2004 | Badarinwa | A61H 39/00 600/26 |
| 2004/0127822 A1 | * | 7/2004 | Eisenberg | A47C 1/06 601/49 |
| 2004/0144790 A1 | * | 7/2004 | Saikali | A61H 37/00 220/592.2 |
| 2005/0086734 A1 | * | 4/2005 | Thies | A45D 19/04 4/516 |
| 2005/0155144 A1 | * | 7/2005 | McDonald | A61H 9/00 4/507 |
| 2005/0205697 A1 | * | 9/2005 | Lo | B05B 1/16 239/592 |
| 2006/0021127 A1 | * | 2/2006 | Li | E04H 4/14 4/507 |
| 2006/0101570 A1 | * | 5/2006 | Kunkel | B05B 17/08 4/507 |
| 2007/0245480 A1 | * | 10/2007 | Sorensen | A61H 33/0087 4/509 |
| 2007/0295327 A1 | * | 12/2007 | Bottomley | A61M 21/00 128/200.14 |
| 2008/0034490 A1 | * | 2/2008 | Li | A61H 33/6063 4/496 |
| 2008/0168599 A1 | * | 7/2008 | Caudill | A61H 33/005 4/541.1 |
| 2008/0222788 A1 | * | 9/2008 | Cunningham | A47K 3/161 4/538 |
| 2009/0222070 A1 | * | 9/2009 | Daffer | A61N 5/0613 607/91 |
| 2009/0289577 A1 | * | 11/2009 | Thursfield | A47K 3/001 315/294 |
| 2010/0005583 A1 | * | 1/2010 | Ton | A61H 35/006 4/541.1 |
| 2011/0004994 A1 | * | 1/2011 | Le | A61H 33/005 4/541.1 |
| 2013/0042402 A1 | * | 2/2013 | Parker | A61H 33/066 4/524 |
| 2013/0152299 A1 | * | 6/2013 | Mizuno | A45D 19/04 4/517 |

* cited by examiner

PORTABLE RELAXATION THERAPY MASSAGE DEVICE FOR THE HEAD

CROSS-REFERENCE TO RELATED APPLICATIONS

This application takes benefit of U.S. Prov. App. 61/877,250 filed 12 Sep. 2013 which is hereby incorporated in its entirety.

FIELD OF THE INVENTION

The present invention relates generally to devices for the administration of fluid therapy and chromotherapy to the head for stimulatory purposes. Particularly, the invention comprises a portable device for administering fluid therapy using pressurized water and/or other therapeutic fluids and/or substances to massage and relax the head and scalp of the user while simultaneously allowing the use of craniofacial chromotherapy thus providing a generally relaxing and refreshing stimulative experience for the head.

BACKGROUND OF THE INVENTION

It is well known that merely standing in a shower with a stream of water directed at one's body results in a stimulating and relaxing effect in and about the area on which the water impinges. Many inventions for applying one or more streams of water to the body are well known in the prior art. Such devices range from mere handheld devices (e.g. a handheld shower massager) through more complex devices that subject the user's entire body to a multiplicity of streams of water and/or steam and/or entrained air (e.g. a therapeutic shower cabinet or whirlpool bath). Moreover, it is well known that variations in the temperature of the impinging water act to vary the stimulative or relaxing effect. Cold water causes one set of sensations, hot water causes another.

These effects are equally effective when applied directly to the head, particularly as a means of decreasing or eliminating head and neck pain and discomfort. A stream of water naturally acts to decrease tension in the muscles of the head and face, thus lessening stress related headaches. Some people report that a hot or warm water spray applied to the head lessens headaches. By the same token, a stream of cold water applied to a greater area of the scalp lowers the temperature of the scalp, thus causing the vasculature of the scalp to constrict slightly. Some people feel this helps alleviate headaches. Other therapeutic effects may be obtained by means of decreasing intra-cranial blood pressure thus preventing and/or treating some forms of stroke and/or facilitating more rapid recovery from cranial concussion. To achieve these effects water and/or other therapeutic fluids and/or substances may be sprayed or misted onto the scalp in a variety of temperatures, from cold to hot. Therapeutic fluids include, but are not limited to, carbonated water, tonic water, and astringent liquids. Therapeutic substances include, but are not limited to ice, bathing salts, and sea salt.

However, no such device exists in the prior art to apply one or more flowing sources of water and/or other therapeutic fluids and/or substances to the head, and only the head of the user. If one wishes to partake of such therapy using devices presently extant in the prior art, one must either take a shower or bath. Obviously, the necessity of disrobing to enjoy these existing therapies adds to their inconvenience.

Similarly, the use of colored light (chromotherapy or light therapy) as a therapeutic regimen is well known in the prior art both to practitioners of Ayurvedic medicine and photobiology. Chromotherapy is variously believed to induce feelings of well-being or "balance" various "energies" in the body (i.e. physical, emotional, spiritual, or mental) and/or treat specific sleep, skin, and mood disorders. While various devices are known in the prior art that combine shower heads, full sized bathtubs, and full-sized shower cabinets with chromotherapeutic devices, none are known that allow selective chromotherapy in the region of the face and neck. Thus, to the extent phototherapy is effective solely when administered through the eyes and the skin of the head and scalp, an apparatus that administers such therapy either independently or in concert with the fluid therapy described above would be advantageous.

By the same token, the use of aromatic substances as a therapeutic regimen is also well known in the prior art. Aromatherapy is variously believed to alter the user's mood or cognitive state, or physical well-being. While various devices are known in the prior art that combine shower, bathtubs, and shower cabinets with aromatherapeutic, none are known that allow selective aromatherapy in the region of the face and neck. Thus, to the extent aromatherapy is effective an apparatus that administers such therapy either independently or in concert with the therapies described above would be advantageous.

Further, to improve the relaxatory effect of the fluid therapy, chromotherapy, and aromatherapy described above, it would be advantageous to use the device in conjunction with a table also equipped with chromotherapeutic light sources.

Thus, it is a first object of the present invention to provide a device that can be used to administer fluid therapy by applying a multiplicity of streams of water and/or other therapeutic fluids and/or substances onto the head, and only the head, of the user. These streams of water and/or other therapeutic fluids and/or substances may be deposited on the scalp and face in any one of a variety of temperatures ranging from hot to cold, or any combination in between. Therapeutic fluids include, but are not limited to, carbonated water, tonic water, and astringent liquids. Therapeutic substances include, but are not limited to, ice, bathing salts, and sea salt.

It is a second object of the present invention to provide a device that can be used to administer chromotherapy to the head of the user. Such chromotherapy is administrable in a variety of colors and intensities—from individual single color therapy to variable color therapy, such colors being derived by varying the intensity of independent red, green, and blue light sources.

It is a third object of the present invention to provide a device that can be used to administer aromatherapy.

It is a fourth object of the present invention to provide a table equipped with chromotherapeutic light sources to enhance the chromotherapeutic effect of the device.

It is a fifth object of the present invention to allow the user to undergo stone or crystal therapy simultaneously while enjoying therapeutic fluid and/or chromotherapy and/or aromatherapy.

SUMMARY OF THE INVENTION

The device is comprised of a cabinet which loosely surrounds the head. The cabinet comprises a top support with a substantially transparent Plexiglas or glass insert and substantially transparent left and right side panels also preferably constructed primarily of Plexiglas or glass. Lamps or LEDs that allow for the administration of chromotherapy are embedded in the edges of the Plexiglas or glass panels comprising the top support and in the rear edges of the left and right side panels such that when activated the Plexiglas or glass insert of the top support and the left and right side panels act as light guides causing the Plexiglas or glass insert of the top support and the left and right side panels to simultaneously glow with the desired color. The base and rear structure of the cabinet rectangular, with the base serving as the repository for water and/or therapeutic substances when the device is used.

The device further comprises a pump to continuously circulate the water and/or therapeutic substances held in the base of the unit up through the rear structure of the unit where they exit through a waterfall spigot onto the forehead of the user and through two adjustable flow lines onto areas of the face chosen by the user.

Constructed into the rear structure of the device is a cavity for containing stones or crystals as might be used in stone therapy. Attached to the rear of the rear structure is a support and cover for an aromatherapy generator unit. Aroma lines duct the generated aromatherapy through the rear structure into the cabinet. Also, the Plexiglas or glass insert mounted in the top support has multiple perforations allowing the placement of another aromatherapy generator on the top support. A pyramidal structure surmounts the top support enclosing this second aromatherapy generator. Installed to the sides and front of the top support is a holder into which a tablet computer may be placed, such that the tablet computer may be used while the user receives fluid and/or chromotherapy and/or aromatherapy. Also installed through the top support is a wireless or wired speaker, preferably a wireless Bluetooth speaker, such that sound from the tablet computer or a cell phone or wireless media steamer may be audibly reproduced.

Since the user must necessarily lay horizontally while using the device, a table is provided. The table comprises a support stand, a reservoir for containing several air-filled or foam cushions or water. Affixed to the inner aspects of the sides of the reservoir are waterproof light strips, preferably LEDs that glow with the desired color. The reservoir may be optionally lined with a colored or colorless transparent or translucent light guide liner to act as a light guide and further enhance the chromotherapeutic effect of the waterproof light strips.

DETAILED DESCRIPTION OF THE INVENTION

Figure 1:
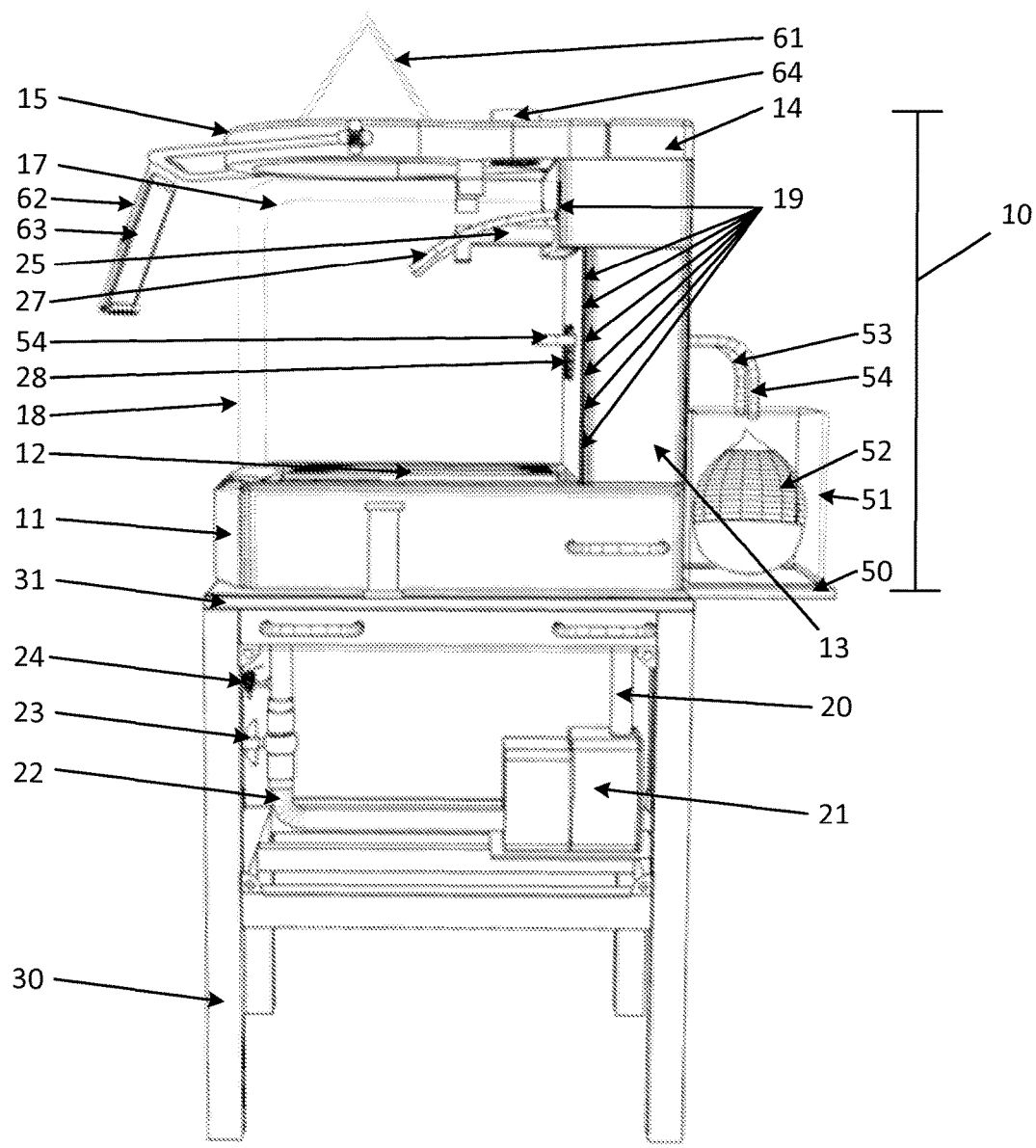
FIG. 1 is a right perspective view of an improved portable relaxation therapy massage device for the head.
Figure 2:
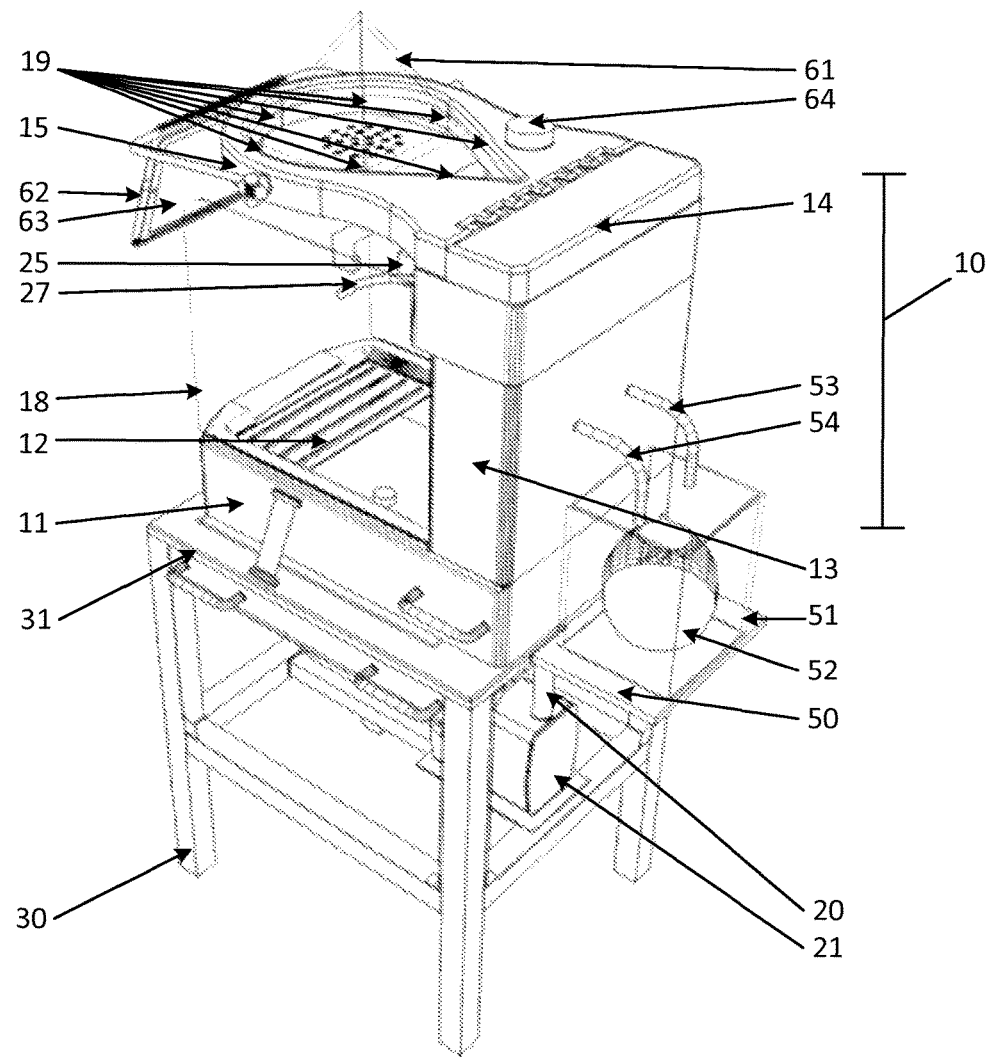
FIG. 2 is a rear-right perspective view of an improved portable relaxation therapy massage device for the head.
Figure 3:
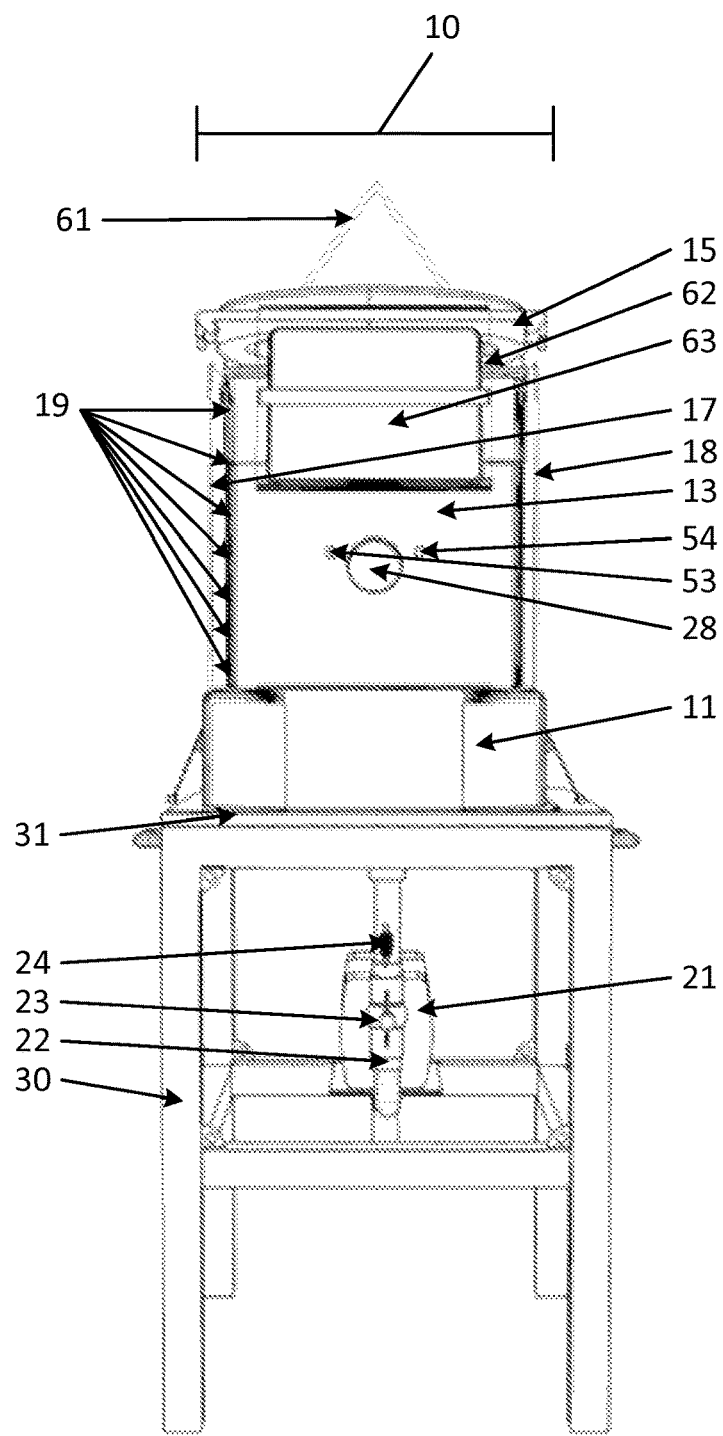
FIG. 3 is a front perspective view of an improved portable relaxation therapy massage device for the head.
Figure 4:
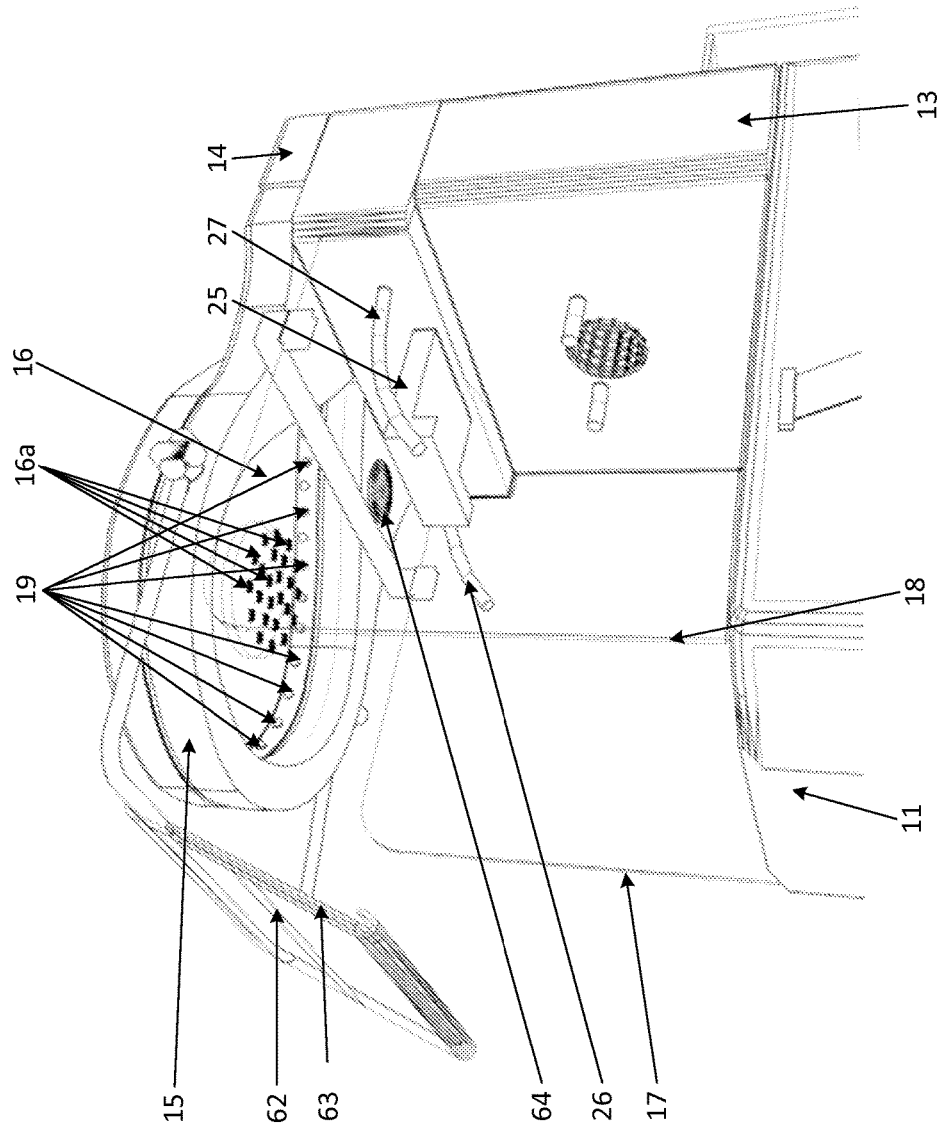
FIG. 4 is a right detail view of the upper aspect of an improved portable relaxation therapy massage device for the head.
Figure 5:
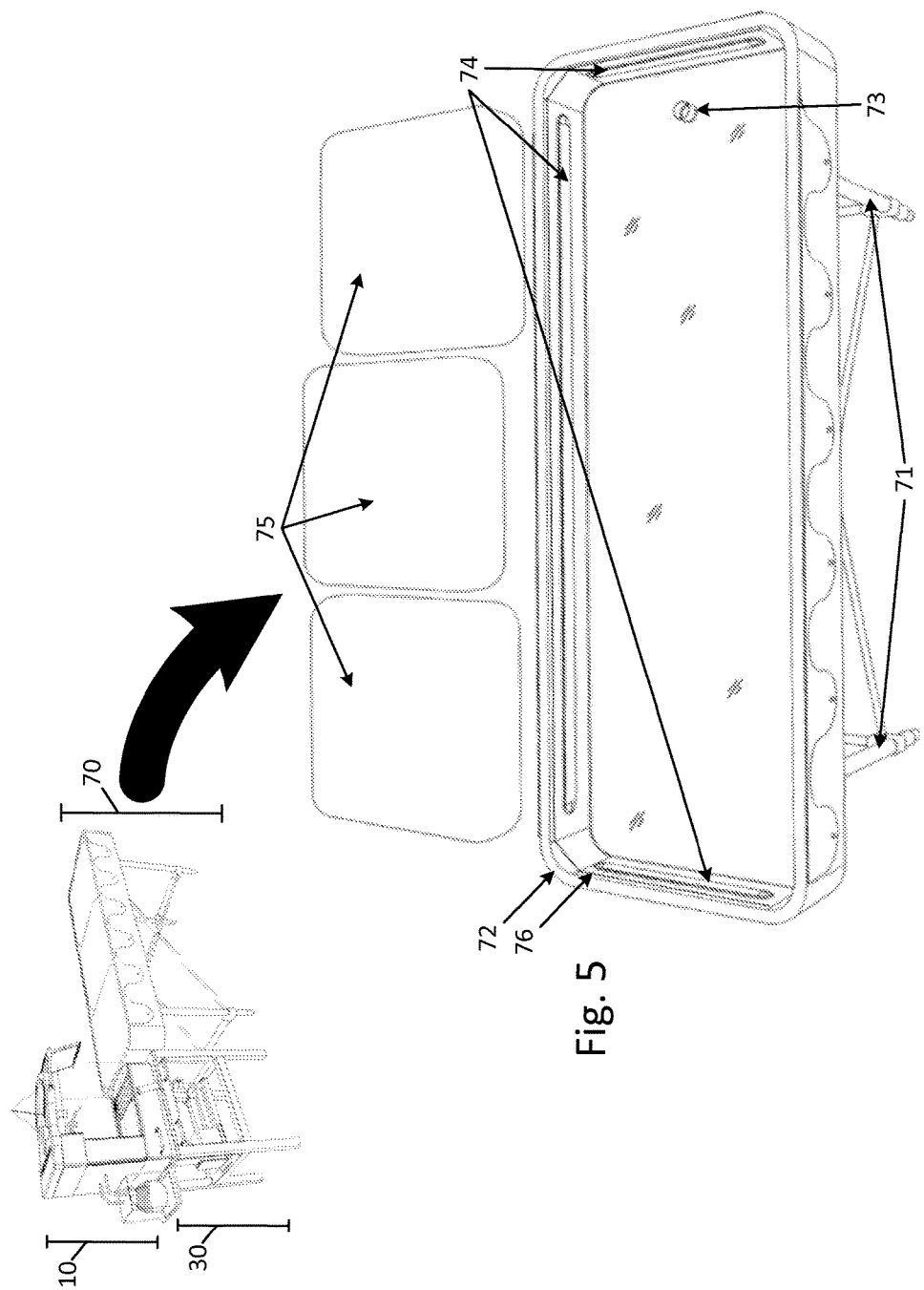
FIG. 5 is a top oblique perspective view of a table for use with an improved portable relaxation therapy massage device for the head.
Figure 6:
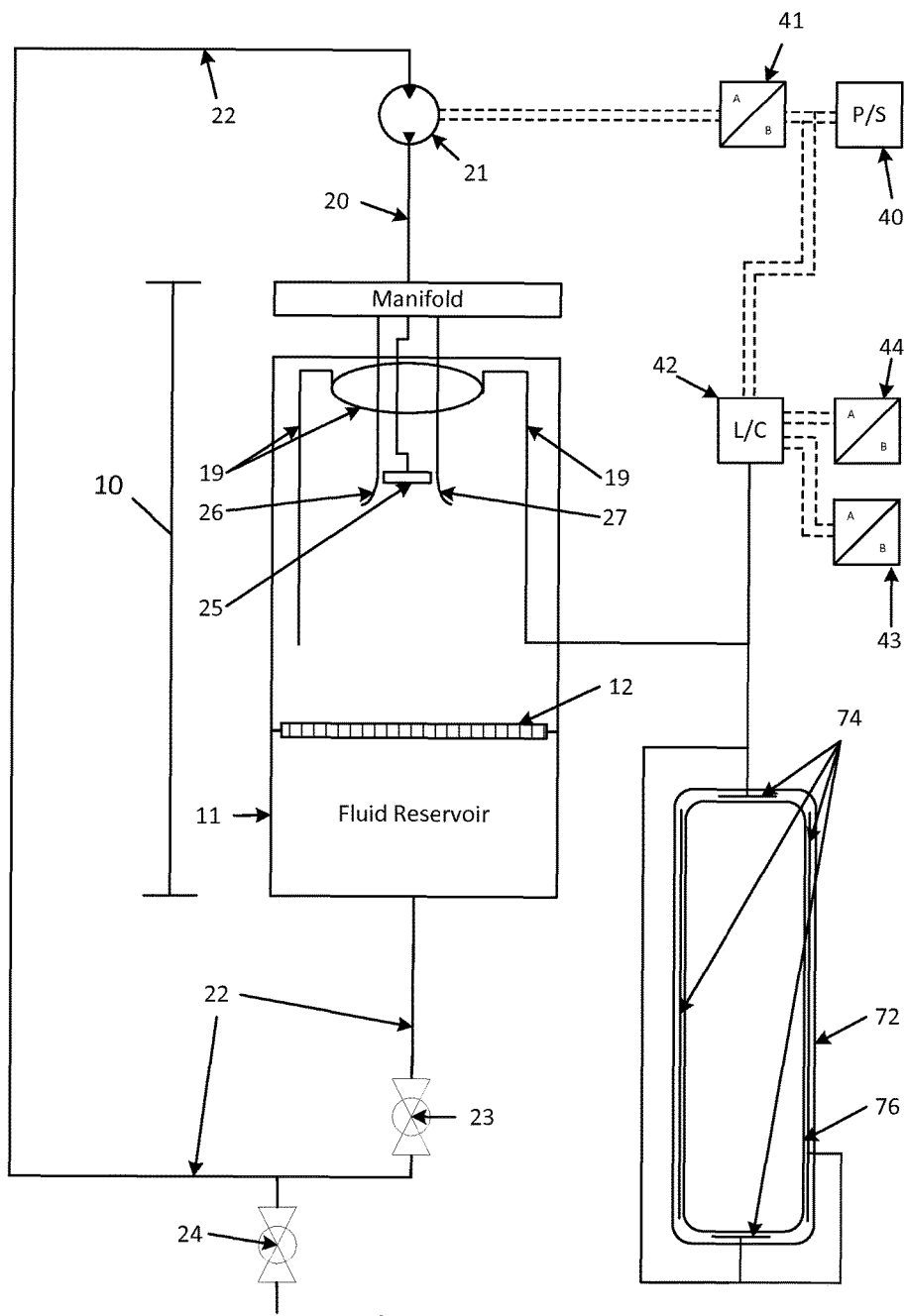
FIG. 6 is a partially schematic view of an improved portable relaxation therapy massage device for the head showing typical electrical and fluid handling components.

Referring now to FIGS. 1 through 6, the device is comprised of a cabinet 10 which loosely surrounds the entire head. Cabinet 10 generally comprised of substantially opaque fluid reservoir 11, rear structure 13, and top support 15 and substantially transparent Plexiglas or glass insert 16 installed in top support 15, left side panel 17, and right side panel 18. A multiplicity of lamps or LEDs 19 that allow for the administration of chromotherapy are installed in the supporting edges of Plexiglas or glass insert 16 and the rear and bottom edges of left and right side panels, 17 and 18 respectively, such that when activated the Plexiglas or glass insert 16 in top support 15, left side panel 17, and right side panel 18 act as light guides causing Plexiglas or glass insert 16 of top support 15, left side panel 17, and right side panel 18 to simultaneously glow with the desired color. Rear structure 13 of cabinet 10 is generally rectangular, substantially hollow prism, containing various aromatherapy and fluid therapy distribution passages. The interior of rear structure 13 is accessible by means of hinged door 14.

On the bottom of the inside aspect of cabinet 10 is drain grate 12 which is ordinarily equipped with a waterproof cushion. Drain grate 12 lets fluid drain into fluid reservoir 11, which then flows by means of gravity through a filter mat into suction feed line 22. The upper part of the inside aspect of rear structure 13 is equipped on the left and right sides by directionally adjustable left flow line 26 and right flow line 27 whereby the user can adjustably direct individual streams of water to different points on the head. Ordinarily two flow lines are sufficient, but those having skill in the art will recognize that more than two may be supplied. Similarly, at the level of left and right flow lines, 26 and 27, respectively, and preferably between them, is waterfall spigot 25. Waterfall spigot 25 is designed so that a nearly continuous sheet of water falls vertically in a plane onto the forehead of the user. This is of course not the only design conceivable. It would be useful to have alternative designs. For example, a waterfall spigot arranged to direct water backwards at an angle towards rear structure 13 and the forehead of the user is helpful to limit splashing in high water volume applications. It will be readily appreciated that other spray/flow patterns are conceivable. All such combinations that produce sprays, drips, mists, and streams are implicitly included in the present disclosure. Left flow line 26, right flow line 27, and waterfall spigot 25 are each in turn connected to a distribution manifold, internally housed in the upper aspect of rear structure 13. The distribution manifold is in turn connected to pressurized feed line 20 which is in turn attached to the output of pump 21.

Constructed into rear structure 13 is stone receptacle 28 for stones or crystals as might be used in stone therapy. Stone receptacle 28 is located adjacent to seventh primary chakra, the Sahasrara, when the user's head is inserted into cabinet 10. By placing the appropriate stones or crystals in stone receptacle 28, the user can enjoy stone therapy.

Attached to the rear of rear structure 13 is support 50 and cover 51. The cavity formed inside cover 51 may be used to enclose a source of aromatherapy such as aromatherapy generator unit 52. Left and right aroma lines, 53 and 54, respectively, duct generated aromatherapy through rear structure 13 and into cabinet 10.

Plexiglas or glass insert 16 mounted in top support 15 has multiple perforations 16a allowing the placement of another aromatherapy generator on top support 15. Pyramidal structure 61 surmounts top support 15 enclosing this second aromatherapy generator. Perforations 16a duct generated aromatherapy through Plexiglas or glass insert 16 and into cabinet 10.

Installed to the sides and front of top support 15 is tablet computer holder 62. Tablet computer 63 may be placed in tablet computer holder 62, such that tablet computer 63 may be used while the user receives fluid and/or chromotherapy and/or aromatherapy.

Also installed through top support 15 is wireless or wired speaker fluid resistant speaker 64, preferably a wireless Bluetooth speaker, such that sound from the tablet computer 63 may be audibly reproduced.

Framework 30 supports cabinet 10 on table top 31. Table top 31 has a drain hole providing a passage for suction feed line 22 such that when fluid is sprayed on the user's head it drains through drain grate 12, into fluid reservoir 11, through a filter mat and into suction feed line 22 and thence to the input of pump 21. Installed in suction feed line 22 is valve 23 used to control the flow of drain water to pump 21. Also, installed in suction feed line 22 is drain cock 24 used to drain used water from fluid reservoir 11.

Pump 21 is electrically wired to power supply 40 operated by means of a pump switch 41. When the user actuates pump switch 41 pump 21 is energized and begins to pump, drawing water and/or other therapeutic fluids and/or substances from the bottom of the fluid reservoir 11 by means of suction feed line 22, through pump 21 and into pressurized feed line 20, into the distribution manifold, and finally out of left and right flow lines, 26 and 27, respectively, and waterfall spigot 25. The water and/or other therapeutic fluids and/or substances fall onto the user's head, flow down through drain grate 12 and into fluid reservoir 11.

LEDs 19 in cabinet 10 can be monochromatic (i.e. all constituent LEDs are the same color) or multi-colored (i.e. each LED can generate a range of colors). LEDs 19 are wired to light control unit 42 that is, in turn, wired to power supply 40 and two controls: 1) Intensity control 43; and, 2) Color control 44. In the case of monochromatic LEDs 19, the user operates intensity control 43 to simultaneously vary the intensity of the light emitted by LEDs 19, thus varying the intensity of the monochromatic light generated inside cabinet 10. In the case of multi-colored LEDs 19, the user operates color control 44 to cause the light control unit 42 to vary the color of LEDs 19 to create a color inside cabinet 10 ranging from no light (black) to red to green to violet to white. If the user selects a color of light, the user then operates intensity control 43 to vary the intensity of the light from dim to bright.

When top support 15 with Plexiglas or glass insert 16 is equipped with Plexiglas or glass pyramidal structure 61, pyramidal structure 61 serves as a light guide and glows with the same color and intensity as Plexiglas or glass insert 16 when illuminated.

Since the user must necessarily lay horizontally while using the device, table 70 is provided. Table 70 generally comprises support stand 71 and table reservoir 72 for containing several cushions 75 or water and/or therapeutic substances. When used with water and/or therapeutic substances, drain 73 is used to drain table reservoir 72 when therapy has been concluded. Drain 73 may be closed by a conventional stopper or valve. Those having skill in the art will recognize that cushions 75 may be air-filled or vinyl encapsulated foam. Affixed to the inner aspects of table reservoir 72 are waterproof light strips 74, preferably comprising LEDs, that glow with the desired color. As before, the LEDs that comprise light strips 74 can be monochromatic (i.e. all constituent LEDs are the same color) or multi-colored (i.e. each LED can generate a range of colors). Also as discussed before, the LEDs comprising light strips 74 are wired to light control unit 42 and operated in tandem with LEDs 19 in cabinet 10. By this means, all LEDs 19 in cabinet 10 the LEDs that comprise light strips 74 in table reservoir 72 may be coordinated to generate chromotherapeutic light as desired. Table reservoir 72 may be optionally lined with a transparent or translucent light guide liner 76 to act as a light guide and further enhance the chromotherapeutic effect of waterproof light strips 74. Light guide liner 76 may be constructed of any suitable glass or plastic material, preferably Plexiglas or styrene, and may be any color including colorless. Further, light guide liner 76 may only cover the inner aspects of the sides of table reservoir 72 or it may cover the entirety of the inner aspect of table reservoir 72.

To operate the device to administer fluid therapy, the user pours water and/or therapeutic fluids and/or substances into fluid reservoir 11. Next, the user places cushions 75 in table reservoir 72. The user then lies on adjoining table 70 and inserts his head, face up, into cabinet 10. The user then rests his head on the waterproof cushion and activates pump 21 via pump switch 41 and enjoys the stimulating and refreshing flow of the water and/or therapeutic fluids and/or other substances present in fluid reservoir 11 as they are expelled onto the user's scalp and face through left and right flow lines, 26 and 27, respectively, and waterfall spigot 25. The water and/or therapeutic fluids and/or substances then drain through drain grate 12, into fluid reservoir 11 and through a filter mat where they travel by means of gravity into suction feed line 22 to pump 21. Pump 21 pressurizes the water and/or therapeutic fluids and/or other substances through pressurized feed line 20, into an internally mounted distribution manifold and thence through left and right flow lines, 26 and 27, respectively, and waterfall spigot 25 to repeat the process.

To operate the device to administer chromotherapy (when the device is equipped with multi-colored LEDs 19 and light strips 74), the user lies on table 70 and inserts his head, face up, into cabinet 10. The user then rests his head on the waterproof cushion and activates light control unit 42 by actuating color control 44 and intensity control 43 to create a colored light inside cabinet 10 and table reservoir 72 of the desired color and intensity.

To operate the device to administer fluid therapy, the user pours water and/or therapeutic fluids and/or substances into fluid reservoir 11. Next, the user places cushions 75 in table reservoir 72. The user then lies on adjoining table 70 and inserts his head, face up, into cabinet 10. The user then rests his head on the waterproof cushion and activates pump 21 via pump switch 41 and enjoys the stimulating and refreshing flow of the water and/or therapeutic fluids and/or other substances present in fluid reservoir 11 as they are expelled onto the user's scalp and face through left and right flow lines, 26 and 27, respectively, and waterfall spigot 25. The water and/or therapeutic fluids and/or substances then drain through drain grate 12, into fluid reservoir 11 and through a filter mat where they travel by means of gravity into suction feed line 22 to pump 21. Pump 21 pressurizes the water and/or therapeutic fluids and/or other substances through pressurized feed line 20, into an internally mounted distribution manifold and thence through left and right flow lines, 26 and 27, respectively, and waterfall spigot 25 to repeat the process. Simultaneously, to operate the device to administer chromotherapy (when the device is equipped with multi-colored LEDs 19 and light strips 74) the user activates light control unit 42 by actuating color control 44 and intensity control 43 to create a colored light inside cabinet 10 and table reservoir 72 of the desired color and intensity.

In another embodiment an electrical device to heat and/or cool the water and/or therapeutic fluids and/or substances in fluid reservoir 11 may be installed in fluid reservoir 11, suction feed line 22, or pressurized feed line 20.

In another embodiment an ultraviolet lamp, or some other means of sterilizing the water and/or therapeutic fluids and/or substances in fluid reservoir 11 may be installed in fluid reservoir 11, suction feed line 22, or pressurized feed line 20.

In another embodiment, a ventilation port for admitting air or other gasses into cabinet 10 is provided. Air may be provided by any of the conventional means, i.e. by a fan or blower and may be warmed by an electrical heating element or cooled by a refrigerated air system. Further, ventilating air may be admixed with oxygen or other compressed gasses to provide an altered atmospheric environment inside cabinet 10.

In another embodiment fluid reservoir 11 may be externally removed from the device and interconnected with cabinet 10 by means of a feed line such that water and/or other therapeutic fluids and/or substances in fluid reservoir 11 are expelled over the head of the user by gravity. In this embodiment, the water and/or other therapeutic fluids and/or substances expelled over the user's head drain directly from the device and into a suitable floor drain.

While the invention has been described in connection with what are considered to be the most practical and preferred embodiments, it is to be understood that the invention is not to be limited to the disclosed embodiments, variants, and sub-variants, but on the contrary is intended to cover various modifications and equivalent arrangements included within the spirit and scope of the disclosure. For example, Plexiglas or glass insert 16 in top support 15 may be an "infinity mirror" such that multiple reflections of LEDs 19 installed at the edge of Plexiglas or glass insert 16 in top support 15 may be perceived. Similarly, it will be readily apparent the phototherapeutic effect of the LEDs 19 and light strips 74 may be enhanced by including one or more effects machines inside or used in conjunction with cabinet 10. For example, a bubble generator or a vapor generator equipped with user selectable or externally controllable sources of colored light may be used to amplify the phototherapeutic effect.

What is claimed is:

1. A portable relaxation therapy device for the head, comprising:
   a) a partially closed cabinet such that when the head is horizontally inserted said cabinet encloses all of the head along five sides of the head;
      i. wherein the interior of said cabinet has at least two directionally adjustable flow lines installed, each of which is fluidically coupled to a fluid distribution manifold;
      ii. wherein the interior of said cabinet has at least one waterfall spigot fluidically coupled to said fluid distribution manifold;
   b) a fluid reservoir fluidically coupled to a suction pickup line;
      i. wherein said suction pickup line is fluidically coupled to the input of a pump;
      ii. wherein the output of said pump is fluidically coupled to a pressurized feed line;
      iii. wherein said pressurized feed line is fluidically coupled to said fluid distribution manifold;
   c) a power supply electrically connected to said pump;
   d) a switch for selectively applying power from said power supply to said pump;
   e) wherein the interior of said cabinet has a stone receptacle containing stones or crystals aligned adjacent to the top of the head when the head is horizontally inserted.

2. The portable relaxation therapy device for the head of claim 1, wherein:
   a) the top, left, and right sides of said cabinet are constructed of a substantially transparent material;
   b) a multiplicity of light emitting diodes (LEDs) are placed along each of the edges of the substantially transparent portions of said top, left, and right sides of said cabinet, such that said substantially transparent portions of said top, left, and right sides of said cabinet act as light guides when said multiplicity of LEDs are illuminated;
   c) a light control unit electrically connected to said multiplicity of LEDs and capable of illuminating them;
   d) wherein said power supply is connected to said light control unit;
   e) a color control electrically connected to said light control unit and capable of causing said light control unit to vary the color of said multiplicity of LEDs; and
   f) an intensity control electrically connected to said light control unit and capable of causing said light control unit to vary the intensity of said multiplicity of LEDs.

3. The portable relaxation therapy device for the head of claim 2, further comprising a support and a cover forming a cavity wherein the cavity inside said cover and above said support is fluidically coupled to the interior of said cabinet by means of at least two aroma lines and a source of aromatherapy is enclosed within said cavity beneath said cover and above said support.

4. The portable relaxation therapy device for the head of claim 2, wherein the substantially transparent portion of said top of said cabinet further comprises a multiplicity of perforations and a pyramidal structure surmounting said top of said cabinet wherein said pyramidal structure acts as a second light guide when said multiplicity of LEDs installed in said substantially transparent portion of said top of said cabinet are illuminated.

5. The portable relaxation therapy device for the head of claim 4, wherein a space beneath said surmounting pyramidal structure and above said substantially transparent portion of said top is fluidically coupled to said cabinet by means of said multiplicity of perforations in said substantially transparent portion of said top.

6. The portable relaxation therapy device for the head of claim 2, further comprising at least one speaker penetrating into said cabinet.

7. The portable relaxation therapy device for the head of claim 2, further comprising at least one speaker penetrating through said top of said cabinet.

8. The portable relaxation therapy device for the head of claim 2, further comprising a tablet computer support.

9. The portable relaxation therapy device for the head of claim 2, further comprising a tablet computer support affixed to said top of said cabinet.

* * * * *